US009872612B2

United States Patent
Komiya et al.

(10) Patent No.: US 9,872,612 B2
(45) Date of Patent: Jan. 23, 2018

(54) ENDOSCOPE REPROCESSOR

(71) Applicant: OLYMPUS CORPORATION, Tokyo (JP)

(72) Inventors: Jiro Komiya, Hachioji (JP); Takaaki Komiya, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 15/384,548

(22) Filed: Dec. 20, 2016

(65) Prior Publication Data

US 2017/0100028 A1    Apr. 13, 2017

Related U.S. Application Data

(63) Continuation of application No. PCT/JP2016/060085, filed on Mar. 29, 2016.

(30) Foreign Application Priority Data

Jun. 4, 2015  (JP) .................................. 2015-114144

(51) Int. Cl.
A61B 1/12    (2006.01)
A61B 1/018   (2006.01)
B08B 9/032   (2006.01)

(52) U.S. Cl.
CPC .............. A61B 1/125 (2013.01); A61B 1/018 (2013.01); A61B 1/123 (2013.01); B08B 9/0325 (2013.01); B08B 9/0328 (2013.01)

(58) Field of Classification Search
CPC .................................................... A61B 1/125
See application file for complete search history.

(56) References Cited

FOREIGN PATENT DOCUMENTS

| JP | H08-000558 A | 1/1996 |
|----|--------------|--------|
| JP | H11-104076 A | 4/1999 |
| JP | 2009-022643 A | 2/2009 |

Primary Examiner — Jason Ko
(74) Attorney, Agent, or Firm — Scully, Scott, Murphy & Presser, P.C.

(57) ABSTRACT

An endoscope reprocessor includes: a first fluid supply section configured to supply a fluid to a forceps plug pipe sleeve of an endoscope; a second fluid supply section configured to supply a fluid to a suction pipe sleeve; and a control section, wherein the control section performs: first control of driving the first fluid supply section and the second fluid supply section at the same time; second control of driving the first fluid supply section such that a flow rate of the second fluid supply section becomes lower than a flow rate of the first fluid supply section; and third control of driving the second fluid supply section such that the flow rate of the first fluid supply section becomes lower than the flow rate of the second fluid supply section after the first control or the second control.

4 Claims, 13 Drawing Sheets

US 9,872,612 B2

ENDOSCOPE REPROCESSOR

CROSS REFERENCE TO RELATED APPLICATION

This application is a continuation application of PCT/JP2016/060085 filed on Mar. 29, 2016 and claims benefit of Japanese Application No. 2015-114144 filed in Japan on Jun. 4, 2015, the entire contents of which are incorporated herein by this reference.

BACKGROUND OF THE INVENTION

1. Field of the Invention

The present invention relates to an endoscope reprocessor.

2. Description of the Related Art

In an endoscope used in a medical field, an insertion portion is inserted into a subject to observe inside of the subject, and a treatment instrument is used to perform a treatment. After use, the endoscope is subjected to processing, such as cleaning/disinfecting of inside of an endoscope conduit, for the next use.

The inside of the endoscope conduit is conventionally cleaned as disclosed for example in Japanese Patent Application Laid-Open Publication No. 11-104076. A cleaning liquid is introduced from a suction pipe sleeve through a cleaning tube and is transmitted through the inside of the endoscope conduit. The cleaning liquid is discharged from a distal end of an insertion portion, and contaminants, such as masses of blood and mucus, attached inside of the endoscope conduit are removed.

SUMMARY OF THE INVENTION

An aspect of the present invention provides an endoscope reprocessor including: a first fluid supply section configured to communicate with a forceps plug pipe sleeve of an endoscope to supply a fluid; a second fluid supply section configured to communicate with a suction pipe sleeve of the endoscope to supply a fluid; and a control section configured to control the first fluid supply section and the second fluid supply section, wherein the control section performs: first control of driving the first fluid supply section and the second fluid supply section at a same time; second control of halting the second fluid supply section or controlling a flow rate of the second fluid supply section to be lower than a flow rate of the first fluid supply section and driving the first fluid supply section; and third control of halting the first fluid supply section or controlling the flow rate of the first fluid supply section to be lower than the flow rate of the second fluid supply section and driving the second fluid supply section after the first control or the second control.

DETAILED DESCRIPTION OF THE PREFERRED EMBODIMENT(S)

Hereinafter, an embodiment of the present invention will be described with reference to the drawings.

(Configuration)

Figure 1:
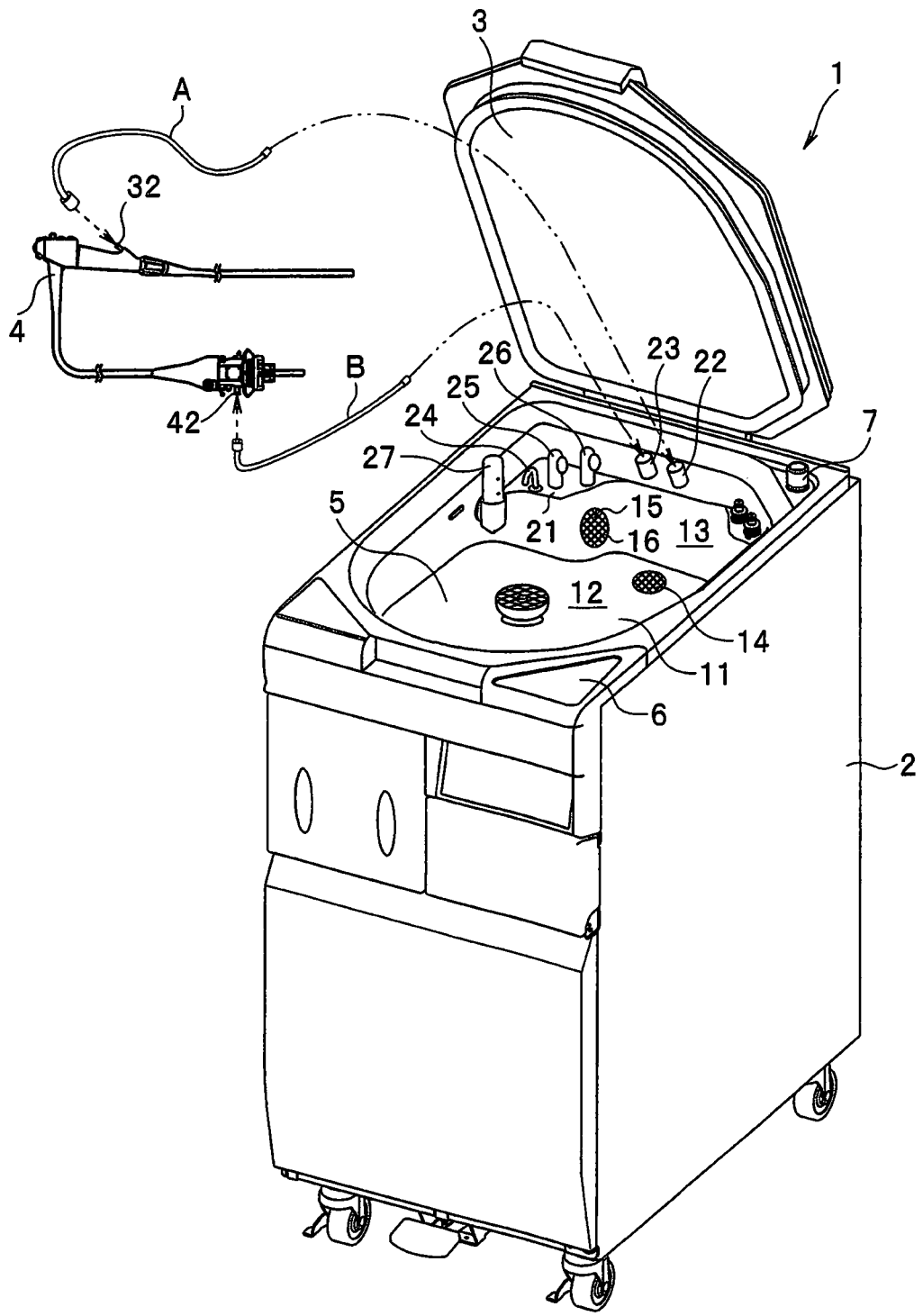
FIG. 1 is a perspective view of an endoscope reprocessor according to an embodiment of the present invention.

FIG. 1 is a perspective view of an endoscope reprocessor according to the embodiment of the present invention.

As shown in FIG. 1, an endoscope reprocessor 1 includes: an apparatus main body 2; and a top cover 3 that can be freely opened and closed. FIG. 1 shows a state that the top cover 3 of the endoscope reprocessor 1 is open.

The endoscope reprocessor 1 is an apparatus configured to execute reprocessing of a contaminated endoscope 4 or endoscope accessories. The reprocessing here is not particularly limited, and the reprocessing may be one or a combination of rinsing by water, cleaning and removing contaminants such as organic matters, disinfecting and neutralizing predetermined microorganisms, and eliminating, killing, or sterilizing all microorganisms.

The apparatus main body 2 includes, on an upper part: a treatment tank 5 for processing of, such as cleaning/disinfecting, of the endoscope 4; an operation panel 6; and a water supply hose connection port 7.

The treatment tank 5 can reserve a liquid, such as a cleaning liquid, water, an alcohol disinfectant liquid, and a sterile liquid. The treatment tank 5 includes an endoscope arrangement portion 11 and a terrace portion 21.

The endoscope arrangement portion 11 includes a bottom portion 12 and a side portion 13 raised up from the bottom portion 12. The endoscope 4 can be arranged, and the liquid can be reserved in the endoscope arrangement portion 11. A discharge port 14 for discharging the reserved liquid is provided on the bottom portion 12 of the endoscope arrangement portion 11. A circulation port 16 including a mesh filter 15 communicating with a liquid pump 51 described later is provided on the side portion 13 of the endoscope arrangement portion 11. Note that the circulation port 16 may be provided on the bottom portion 12, instead of the side portion 13 of the endoscope arrangement portion 11.

The terrace portion 21 is provided adjacent to the endoscope arrangement portion 11, at a position one stage higher than the endoscope arrangement portion 11. The terrace portion 21 includes: a forceps plug port 22 that is a cleaning tube connection port; a suction pipe sleeve port 23 that is a cleaning tube connection port; a cleaning agent nozzle 24; a disinfectant liquid nozzle 25; a water supply circulation nozzle 26; and a water level sensor 27.

The forceps plug port 22 is a port for connecting a connector a1 of a cleaning tube A. In the cleaning tube A, the connector a1 provided on one end can be connected to the forceps plug port 22 of the endoscope reprocessor 1, and a connector a2 provided on the other end can be connected to a forceps plug pipe sleeve 32 of the endoscope 4. The forceps plug port 22 can communicate with the forceps plug pipe sleeve 32 of the endoscope 4 through the cleaning tube A.

The suction pipe sleeve port 23 is a port for connecting a connector b1 of the cleaning tube B. In the cleaning tube B, the connector b1 provided on one end can be connected to the suction pipe sleeve port 23 of the endoscope reprocessor 1, and a connector b2 provided on the other end can be connected to a suction pipe sleeve 42 of the endoscope 4. The suction pipe sleeve port 23 can communicate with the suction pipe sleeve 42 of the endoscope 4 through the cleaning tube B.

Note that although the endoscope reprocessor 1 includes the forceps plug port 22 and the suction pipe sleeve port 23 in FIG. 1, the number of ports is not limited to two, but may be more than two.

The cleaning agent nozzle 24 can supply a cleaning liquid to the treatment tank 5. The disinfectant liquid nozzle 25 can supply a disinfectant liquid to the treatment tank 5. The water supply circulation nozzle 26 can supply water imported from the water supply hose connection port 7 described later to the treatment tank 5 and can again supply and circulate, in the treatment tank 5, the liquid of the treatment tank 5 imported from the circulation port 16 including the mesh filter 15. The water level sensor 27 can detect a water level of the liquid reserved in the treatment tank 5.

The operation panel 6 is arranged on a front part of the upper part of the endoscope reprocessor 1. The operation panel 6 includes various operation buttons not shown. A user can give various instructions to the endoscope reprocessor 1 through the operation panel 6.

The water supply hose connection port 7 is provided on a back part of the upper part of the endoscope reprocessor 1. A water supply hose connected to a water faucet not shown is connected to the water supply hose connection port 7, and water can be supplied to the endoscope reprocessor 1 through the water supply circulation nozzle 26.

The top cover 3 is provided on the upper part of the apparatus main body 2, and the top cover 3 can be opened and closed. In the endoscope reprocessor 1, the top cover 3 is put into an open state, and the endoscope 4 is arranged on the endoscope arrangement portion 11. The endoscope 4 and the endoscope reprocessor 1 are connected by the cleaning tube A and the cleaning tube B, and the endoscope 4 is set on the treatment tank 5. The top cover 3 is put into a closed state after the endoscope 4 is set, and the endoscope reprocessor 1 enters a state in which processing, such as cleaning/disinfecting, can be executed.

Subsequently, an internal configuration of the endoscope reprocessor 1 of the present embodiment will be described with reference to FIG. 2.

Figure 2:
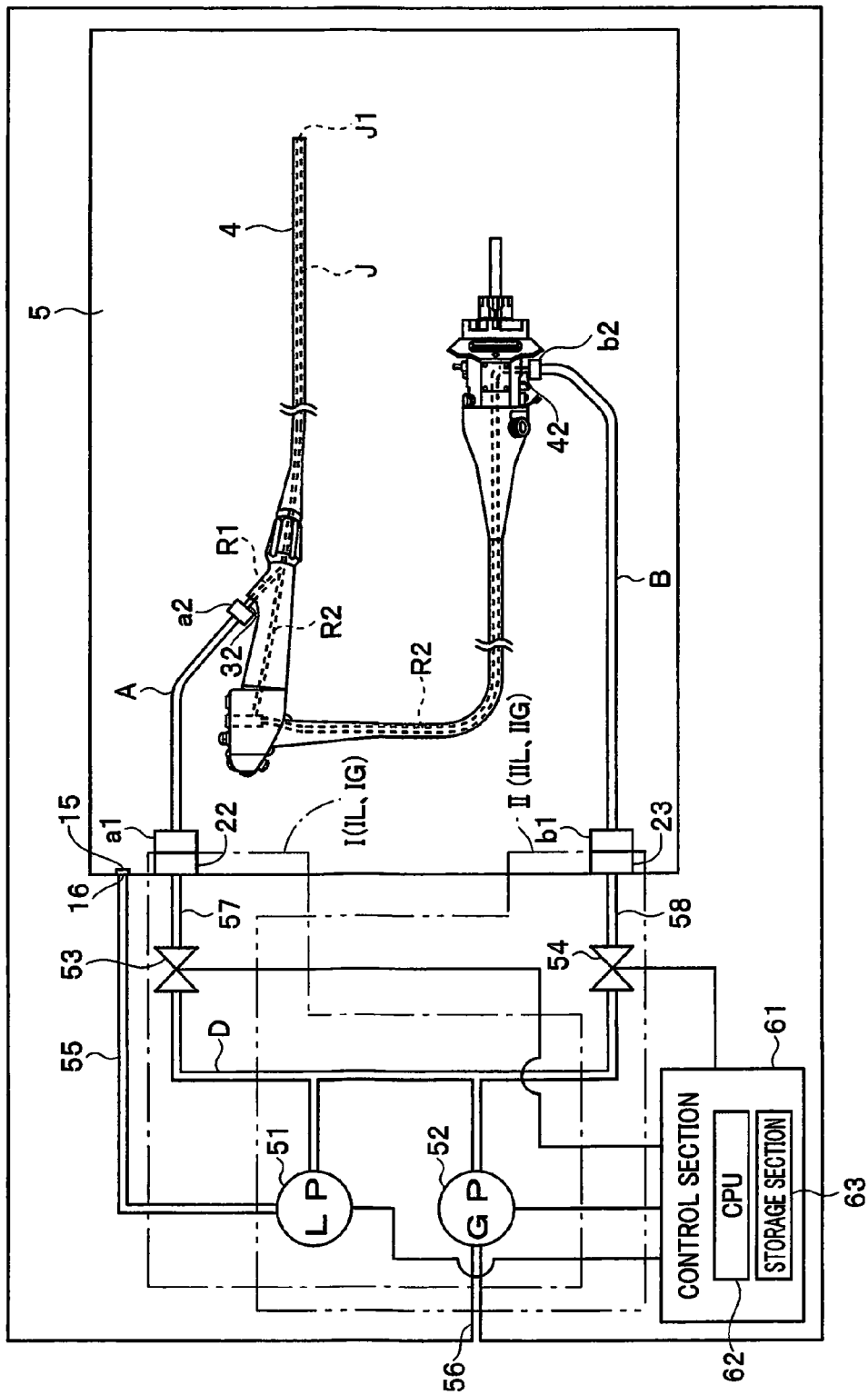
FIG. 2 is a configuration diagram of main parts of the endoscope reprocessor according to the embodiment of the present invention.

FIG. 2 is a configuration diagram of main parts of the endoscope reprocessor 1 according to the embodiment of the present invention. FIG. 2 shows a state that the endoscope 4 is connected to the endoscope reprocessor 1 by the cleaning tube A and the cleaning tube B. Note that FIG. 2 does not illustrate components other than the main parts of the endoscope reprocessor 1.

As shown in FIG. 2, the endoscope reprocessor 1 includes the liquid pump 51, a gas pump 52, the treatment tank 5, a first electromagnetic valve 53, a second electromagnetic valve 54, the forceps plug port 22, the suction pipe sleeve port 23, and a control section 61.

The liquid pump 51 can import a liquid, such as a cleaning liquid, of the treatment tank 5 from a conduit 55 and the circulation port 16 including the mesh filter 15. The liquid pump 51 can pressurize the imported liquid with a predetermined pressure and transmit the pressurized liquid to a branch conduit D. The mesh filter 15 can filter contaminants P flown down from the inside of the conduit of the endoscope 4 and floating in the liquid, such as a cleaning liquid, in the treatment tank 5.

The gas pump 52 can import a gas through a conduit 56. The gas pump 52 can pressurize the imported gas with a predetermined pressure and feed the pressurized gas to the branch conduit D. In the present embodiment, air is imported as the gas.

Each of the first electromagnetic valve 53 and the second electromagnetic valve 54 is electrically connected to the control section 61 and can switch a valve to an open state or a closed state based on a control signal received from the control section 61.

The liquid pump 51, the branch conduit D, the first electromagnetic valve 53, a conduit 57, and the forceps plug port 22 configure a first liquid supply section IL. The liquid pump 51 is connected to the first electromagnetic valve 53 through the branch conduit D. The first electromagnetic valve 53 is then connected to the forceps plug port 22 through the conduit 57. The cleaning tube A can connect the connector a1 to the forceps plug port 22 and can connect the connector a2 described later to the forceps plug pipe sleeve 32 of the endoscope 4. By connecting the forceps plug port 22 and the forceps plug pipe sleeve 32 by the cleaning tube A and putting the first electromagnetic valve 53 into the open state, the liquid pump 51 is connected to the forceps plug pipe sleeve 32 of the endoscope 4. As a result, the first liquid supply section IL can supply the liquid into the conduit of the endoscope 4 from the forceps plug pipe sleeve 32.

The liquid pump 51, the branch conduit D, the second electromagnetic valve 54, a conduit 58, and the suction pipe sleeve port 23 configure a second liquid supply section IIL. The liquid pump 51 is connected to the second electromagnetic valve 54 through the branch conduit D. The second electromagnetic valve 54 is then connected to the suction pipe sleeve port 23 through the conduit 58. The cleaning tube B can connect the connector b1 to the suction pipe sleeve port 23 and can connect the connector b2 to a pipe sleeve of the suction pipe sleeve port 23 of the endoscope 4. By connecting the suction pipe sleeve port 23 and the suction pipe sleeve 42 by the cleaning tube B and putting the second electromagnetic valve 54 into the open state, the liquid pump 51 is connected to the suction pipe sleeve 42 of the endoscope 4. As a result, the second liquid supply section IIL can supply the liquid into the conduit of the endoscope 4 from the suction pipe sleeve 42.

The gas pump 52, the branch conduit D, the first electromagnetic valve 53, the conduit 57, and the forceps plug port 22 configure a first gas supply section IG. The gas pump 52 is connected to the first electromagnetic valve 53 through the branch conduit D. The first electromagnetic valve 53 is then connected to the forceps plug port 22 through the conduit 57. By connecting the forceps plug port 22 and the forceps plug pipe sleeve 32 by the cleaning tube A and putting the first electromagnetic valve 53 into the open state, the gas pump 52 is connected to the forceps plug pipe sleeve 32 of the endoscope 4 through the first electromagnetic valve 53. As a result, the first gas supply section IG can supply the gas into the conduit of the endoscope 4 from the forceps plug pipe sleeve 32.

The gas pump 52, the branch conduit D, the second electromagnetic valve 54, the conduit 58, and the suction pipe sleeve port 23 configure a second gas supply section IIG. The gas pump 52 is connected to the second electromagnetic valve 54 through the branch conduit D. The second electromagnetic valve 54 is then connected to the suction pipe sleeve port 23 through the conduit 58. By connecting the suction pipe sleeve port 23 and the suction pipe sleeve 42 by the cleaning tube B and putting the second electromagnetic valve 54 into the open state, the gas pump 52 is connected to the suction pipe sleeve 42 of the endoscope 4 through the second electromagnetic valve 54. As a result, the second gas supply section IIG can supply the gas into the conduit of the endoscope 4 from the suction pipe sleeve 42.

The first liquid supply section IL and the first gas supply section IG configure a first fluid supply section I configured to communicate with the forceps plug pipe sleeve 32 of the endoscope 4 to supply a fluid (I of FIG. 2).

The second liquid supply section IIL and the second gas supply section IIG configure a second fluid supply section II configured to communicate with the suction pipe sleeve 42 of the endoscope 4 to supply a fluid (II of FIG. 2).

In the present embodiment, the first fluid supply section I and the second fluid supply section II share the liquid pump 51 and the gas pump 52. However, the present invention is not limited to this, and each of the first fluid supply section I and the second fluid supply section II may include a liquid pump and a gas pump.

The control section 61 can include a central processing unit (hereinafter, called "CPU 62") and a storage section 63 including a ROM, a RAM, or the like.

The control section 61 is electrically connected to the liquid pump 51, the gas pump 52, the first electromagnetic valve 53, and the second electromagnetic valve 54. The control section 61 can control the drive of the liquid pump 51 and the gas pump 52 and the opening and closing operation of the first electromagnetic valve 53 and the second electromagnetic valve 54 to control the first fluid supply section I and the second fluid supply section II.

The functions of the control section 61 are realized by the CPU 62 reading and executing programs corresponding to the respective processing sections from the storage section 63.

The control section 61 performs first control of driving the first fluid supply section I and the second fluid supply section II at the same time. In the first control, the second electromagnetic valve 54 is opened more than during second control described later, and the flow rate is increased. In the first control, the first electromagnetic valve 53 is opened more than during third control described later, and the flow rate is increased.

The control section 61 performs the second control of halting the second fluid supply section II, controlling the flow rate to be lower than the flow rate of the first fluid supply section I, and driving the first fluid supply section I.

When the first fluid supply section I and the second fluid supply section II share the liquid pump 51 and the gas pump 52 as in the present embodiment, "halting the second fluid supply section II" denotes a state in which the liquid pump 51 and the gas pump 52 are in the drive state, but the second electromagnetic valve 54 is closed. "Controlling the flow rate to be lower than the flow rate of the first fluid supply section I" denotes a state in which the liquid pump 51 and the gas pump 52 are in the drive state, but the second electromagnetic valve 54 is narrowed more than the first electromagnetic valve 53.

The control section 61 may perform a gas-liquid two-phase flow as the second control.

The gas-liquid two-phase flow denotes a state in which the air is fed from the gas pump 52 in the state that the conduit of the endoscope 4 is filled with the liquid, and the liquid and the gas coexist in the conduit of the endoscope 4. More specifically, the gas-liquid two-phase flow includes any of a state that bubbles exist in the liquid, a state that droplets exist in the gas, and a state that masses of the liquid and masses of the gas exist side by side.

When the control section 61 performs the gas-liquid two-phase flow as the second control, the control section 61 drives the first liquid supply section IL to fill the conduit of the endoscope 4 with the liquid and then drives the first gas supply section IG in the state that the second fluid supply section II is halted to push out the liquid by the gas. As a result, the gas supplied from the first gas supply section IG into the conduit of the endoscope 4 and the liquid in the conduit of the endoscope 4 coexist, and this is a so-called gas-liquid two-phase flow state.

The control section 61 performs the third control of halting the first fluid supply section I or controlling the flow rate to be lower than the flow rate of the second fluid supply section II and driving the second fluid supply section II.

When the first fluid supply section I and the second fluid supply section II share the liquid pump 51 and the gas pump 52 as in the present embodiment, "halting the first fluid supply section I" denotes a state in which the liquid pump 51 and the gas pump 52 are in the drive state, but the first electromagnetic valve 53 is closed. "Controlling the flow rate to be lower than the flow rate of the second fluid supply section II" denotes a state in which the liquid pump 51 and the gas pump 52 are in the drive state, but the first electromagnetic valve 53 is narrowed more than the second electromagnetic valve 54.

The control section 61 may perform a gas-liquid two-phase flow as the third control.

When the control section 61 performs the gas-liquid two-phase flow as the third control, the control section 61 drives the second liquid supply section IIL to fill the conduit of the endoscope 4 with the liquid and then drives the second gas supply section IIG in the state that the first fluid supply section I is halted to push out the liquid by the gas. As a result, a so-called gas-liquid two-phase flow can be supplied, in which the gas supplied from the second gas supply section IIG into the conduit of the endoscope 4 and the liquid in the conduit of the endoscope 4 coexist.

The endoscope 4 includes: a treatment instrument channel J in which the forceps plug pipe sleeve 32 is formed on one end; and a suction conduit R2 in which the suction pipe sleeve 42 is formed on one end. The other end of the suction conduit R2 is coupled to a middle position of the treatment instrument channel J. In the present invention, a conduit part from the part of the coupling of the suction conduit R2 to the forceps plug pipe sleeve 32 in the treatment instrument channel J is called a treatment instrument channel proximal end side R1.

The forceps plug pipe sleeve 32 can be connected to the connector a2 of the cleaning tube A.

The suction pipe sleeve 42 can be connected to the connector b2 of the cleaning tube B.

Figure 3:
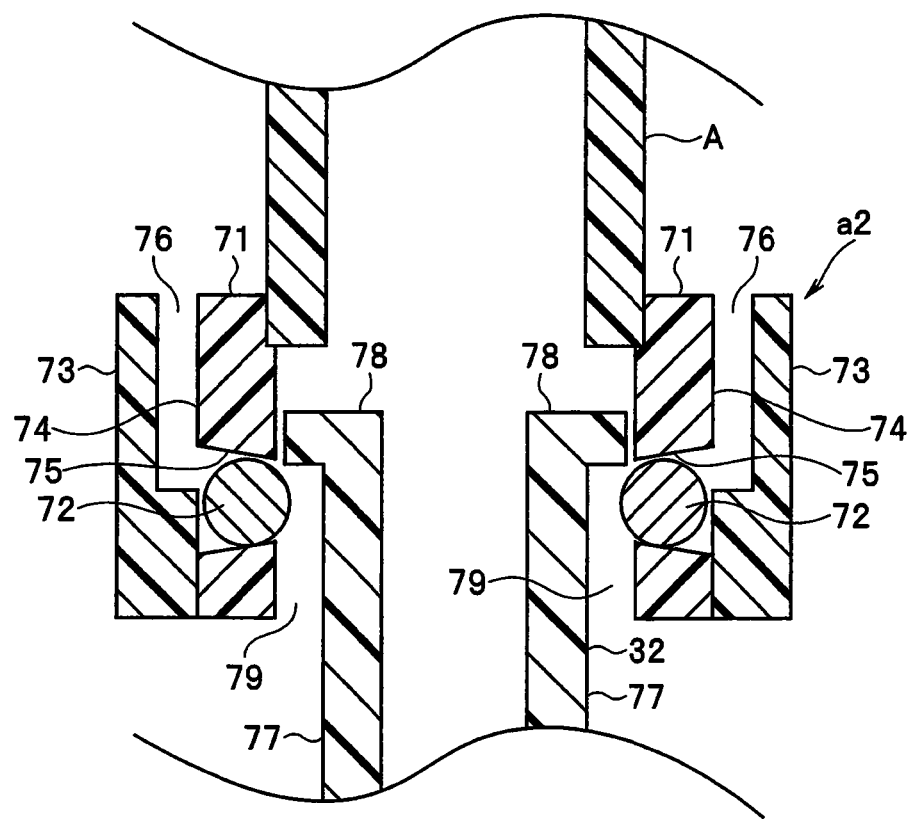
FIG. 3 is a schematic diagram of a bonding part of a connector of a cleaning tube of the endoscope reprocessor and a forceps plug pipe sleeve according to the embodiment of the present invention.

FIG. 3 is a schematic diagram of a bonding part of the connector a2 of the cleaning tube A of the endoscope reprocessor 1 and the forceps plug pipe sleeve 32 according to the embodiment of the present invention.

Subsequently, the bonding part of the connector a2 of the cleaning tube A and the forceps plug pipe sleeve 32 of the endoscope 4 will be described.

The connector a2 of the cleaning tube A includes: a connector main body 71 provided on a distal end of the cleaning tube A; a plurality of spheres 72; and a connector cover 73 provided on an outer circumference portion of the connector main body 71.

The connector main body 71 is configured by a material such as plastic. The connector main body 71 is cylindrical and includes a plurality of circular holes 75 on a peripheral side portion 74. Four circular holes 75 are provided at equal intervals in a circumferential direction on the peripheral side portion 74 of the connector main body 71, for example. Each of the circular holes 75 is formed in a tapered shape in the cross section of the peripheral side portion 74 in a thickness direction such that the diameter decreases from an outer circumference surface toward an inner circumference surface of the connector main body 71.

The plurality of spheres 72 are configured by a material such as metal. The diameter of the plurality of spheres 72 is larger than that of the circular holes 75 on the inner circumference surface of the peripheral side portion 74 to prevent dropping out from the inner circumference surface of the peripheral side portion 74, and the plurality of spheres 72 are arranged such that part of the plurality of spheres 72 is in the circular holes 75.

The connector cover 73 is configured by a material such as plastic. The connector cover 73 is arranged outside of the connector main body 71 on which the plurality of spheres 72 are arranged. A circumferential gap 76 is formed between the connector cover 73 and the connector main body 71.

The forceps plug pipe sleeve 32 is configured by a material, such as metal and a resin. The forceps plug pipe sleeve 32 is configured by forming a body portion 77 in a cylindrical shape and including an outward flange 78 on a distal end.

The connector a2 of the cleaning tube A is detachably attached to the forceps plug pipe sleeve 32.

In the state that the connector a2 is attached to the forceps plug pipe sleeve 32, the plurality of (four here) spheres 72 of the connector a2 lock the outward flange 78 of the forceps plug pipe sleeve 32 so that the outward flange 78 does not drop out. A circumferential gap 79 is formed between the body portion 77 of the forceps plug pipe sleeve 32 and the connector main body 71.

The liquid, such as a cleaning liquid, transmitted from the cleaning tube A is introduced to the inside of the body portion 77 of the forceps plug pipe sleeve 32, and the fluid flows out from the gap 76 through between the connector main body 71 and the forceps plug pipe sleeve 32. The liquid flows out from the gap 79 through between the circular holes 75 and the spheres 72, and the forceps plug pipe sleeve 32 can be cleaned.

Figure 10:
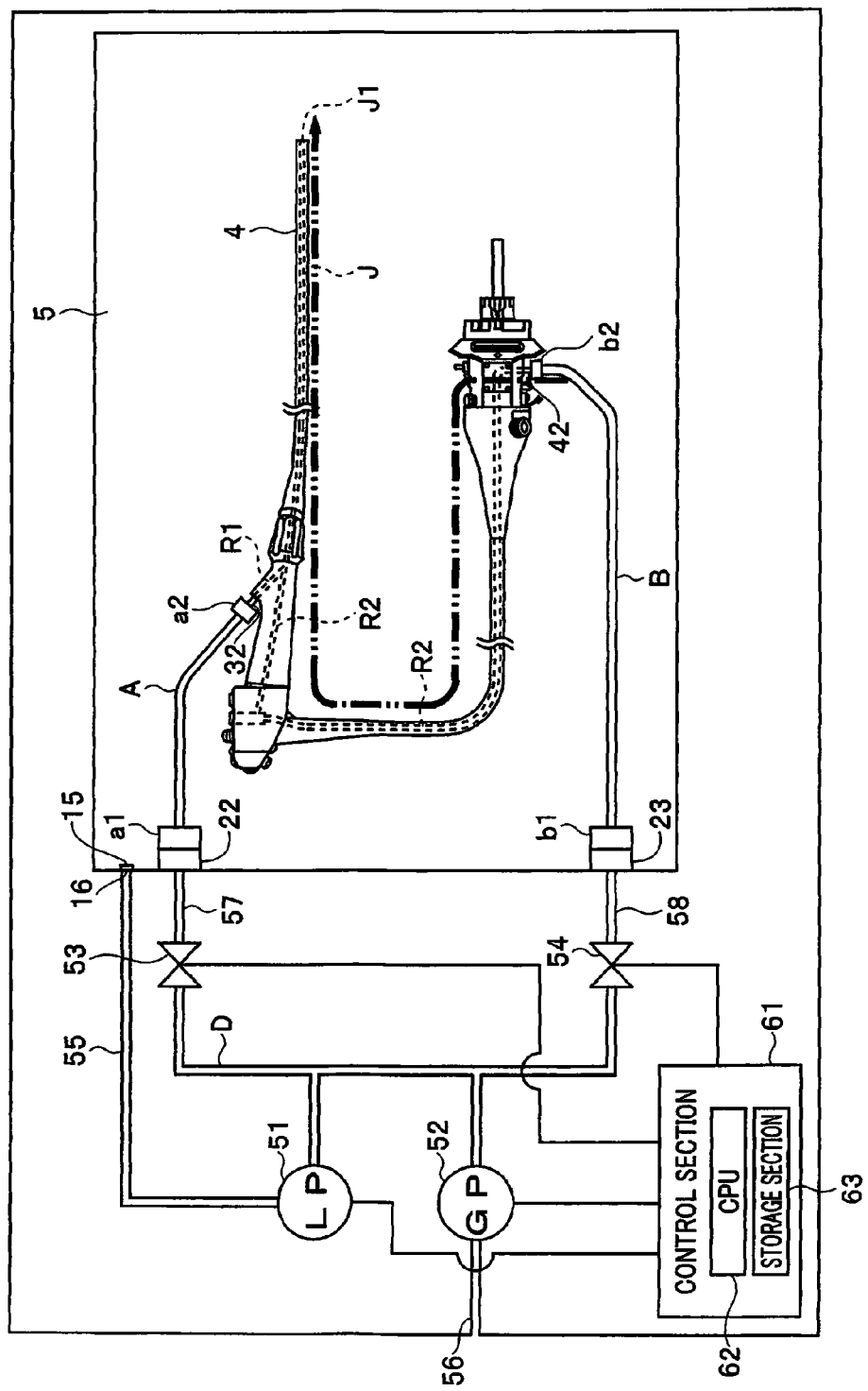
FIG. 10 is an explanatory view describing third control of the endoscope reprocessor according to the embodiment of the present invention.

Note that the shape of the connector a2 of the cleaning tube A is not limited to the one described above in the present invention, and for example, a connector disclosed in FIG. 10 of Japanese Patent No. 5676057 can also be applied.

(Action)

Next, a cleaning process will be described as an action of the endoscope reprocessor 1.

The user opens the top cover 3 of the endoscope reprocessor 1 and sets the endoscope 4 to be cleaned on the endoscope reprocessor 1. More specifically, the user connects the connector a1 of the cleaning tube A to the forceps plug port 22 and connects the connector a2 to the forceps plug pipe sleeve 32 of the endoscope 4. The user connects the connector b1 of the cleaning tube B to the suction pipe sleeve port 23 and connects the connector b2 to the suction pipe sleeve 42 of the endoscope 4. Note that although not shown, other than the connection using the cleaning tube A and the cleaning tube B, a tube is used to connect the endoscope reprocessor 1 and the endoscope 4 as necessary.

After the endoscope reprocessor 1 and the endoscope 4 are connected, the user arranges the endoscope 4 on the endoscope arrangement portion 11 and puts the top cover 3 into the closed state.

When the user issues a starting instruction of a process of cleaning/disinfecting or the like from the operation panel 6, the CPU 62 reads a predetermined program from the storage section 63 and starts the process of the program.

Figure 4:
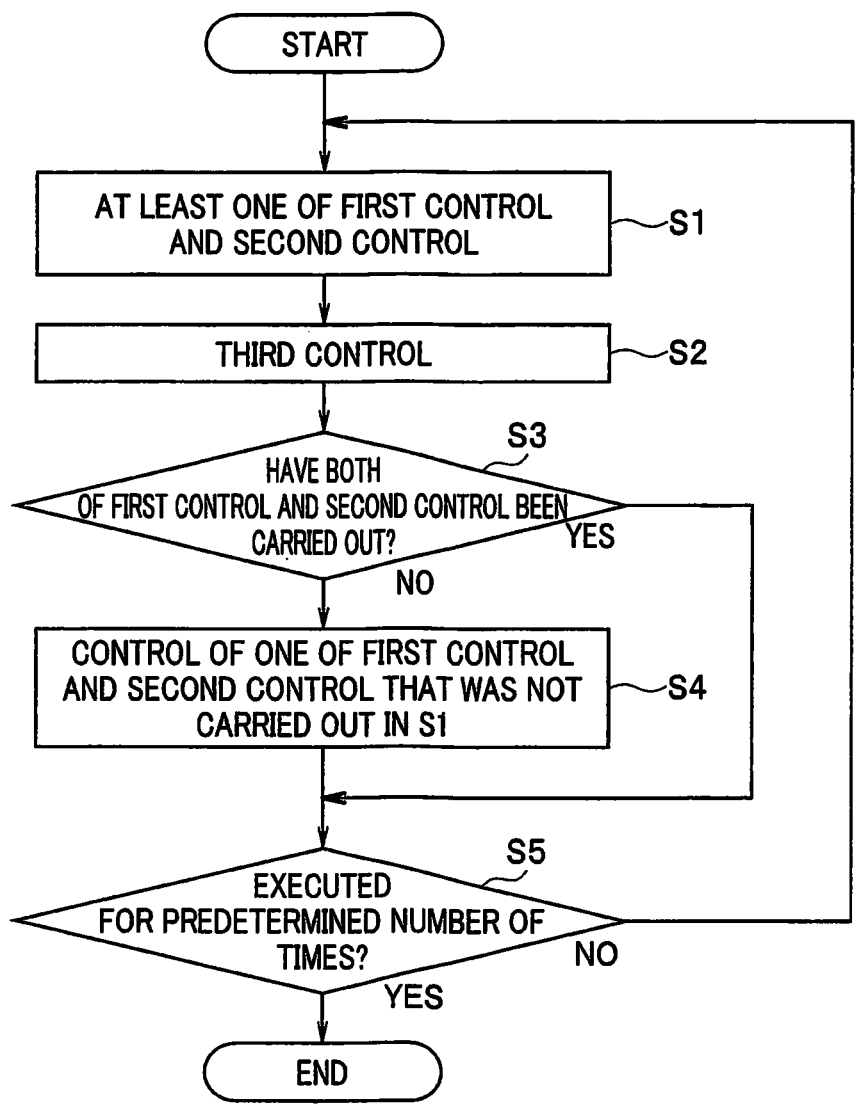
FIG. 4 is a flowchart showing fluid transmission patterns of the endoscope reprocessor according to the embodiment of the present invention.
Figure 5:
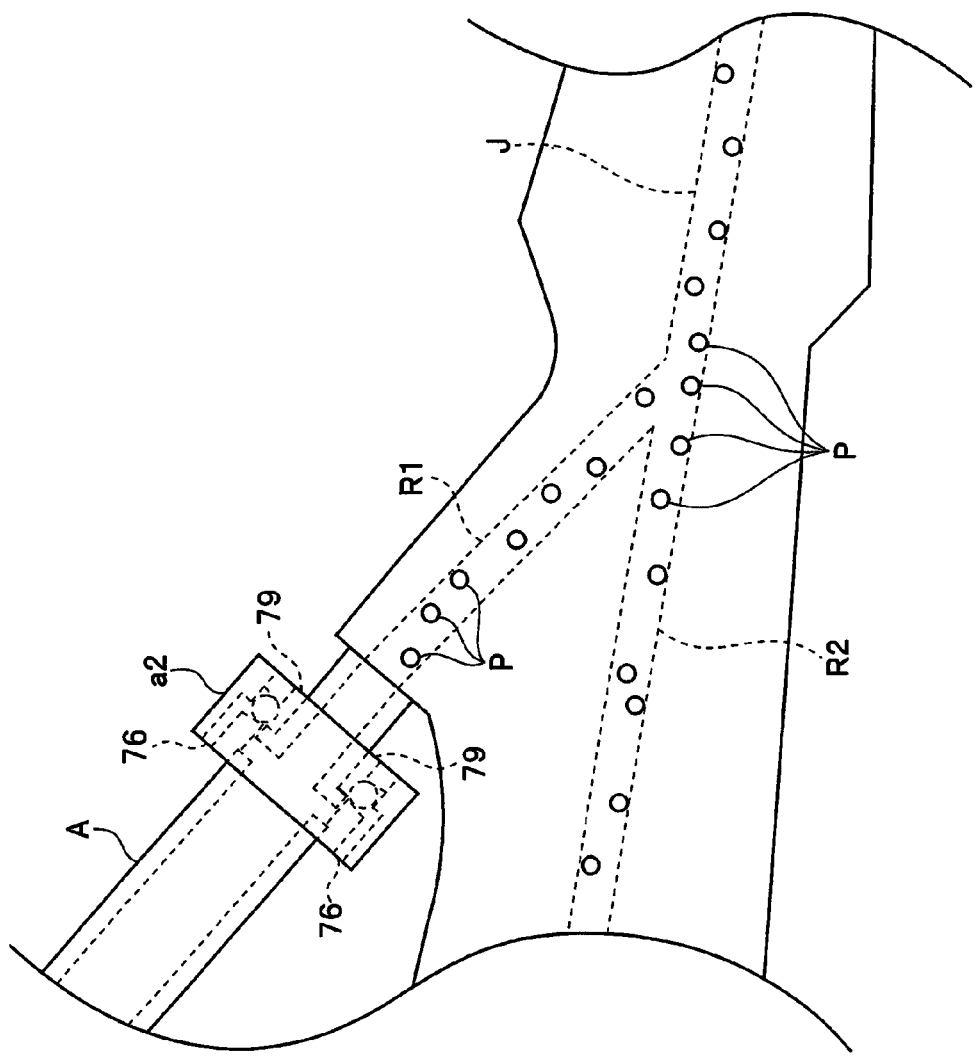
FIG. 5 is an enlarged view enlarging a merging section in the endoscope reprocessor according to the embodiment of the present invention.

FIG. 4 is a diagram showing fluid transmission patterns that can be adopted in the present invention. FIGS. 5, 7, 9, 11, 12, and 13 are enlarged explanatory views of a merging section for describing fluid transmission based on the first control of the endoscope reprocessor 1 according to the embodiment of the present invention.

In the present invention, before the third control is carried out (S2), at least one of the first control and the second control is carried out (S1). By carrying out the first control or the second control (S1) before carrying out the third control (S2), the wastes P existing in the region of R1 of FIG. 5 can be removed to prevent the wastes P existing in the region of R1 at the execution of the third control from being caught between the forceps plug pipe sleeve 32 and the cleaning tube A.

Which one of the first control and the second control is carried out in S1 is not limited. When both of the first control and the second control are carried out in S1, which one is carried out first is not limited.

When one of the first control and the second control is not carried out in S1, it is preferable to carry out the control that was not carried out (S3, S4), after the third control is carried out (S2).

Specifically, the fluid transmission patterns can include the following six patterns.

(Pattern 1)

The control section 61 sequentially controls the first control, the second control, and the third control.

(Pattern 2)

The control section 61 sequentially controls the first control, the third control, and the second control.

(Pattern 3)

The control section 61 sequentially controls the second control, the first control, and the third control.

(Pattern 4)

The control section 61 sequentially controls the second control, the third control, and the first control.

(Pattern 5)

The control section 61 sequentially controls the first control and the third control and does not carry out the second control.

(Pattern 6)

The control section 61 sequentially controls the second control and the third control and does not carry out the first control.

Although any of the patterns are preferable in the present invention, the patterns 1, 2, 3, and 4 are preferable. The patterns 1, 3, and 4 are more preferable, and the pattern 1 is more preferable. A flow shown in FIG. 4 is a flow diagram of the patterns 1 to 4.

The control section 61 determines whether the cleaning process from S1 to S3 or from S1 to S4 is executed for a predetermined number of times, and if the cleaning process is not executed for the predetermined number of times (S5: NO), the process returns to S1. If the control section 61 judges that the cleaning process is executed for the predetermined number of times, the processing of the cleaning process ends (S5: YES).

It is only necessary that the predetermined number of times is one or more, and it is more preferable that the predetermined number of times is four.

When the predetermined number of times is two or more, the same pattern among the patterns 1 to 4 may be repeated, or different patterns may be combined.

The process may move to the next control or the next step after one control is repeated for a plurality of times in S1, S2, or S4.

When both of the first control and the second control are carried out in S1 or S4, the process may move to the next step after the first control and the second control are alternately carried out.

Note that although not shown in the flow of FIG. 4, the process may return to S1 after S2 or may return to S2 after S3.

Control for another purpose may be carried out between the respective controls. An example of the control for another purpose includes control of applying alcohol to the conduit for the purpose of drying.

Figure 6:
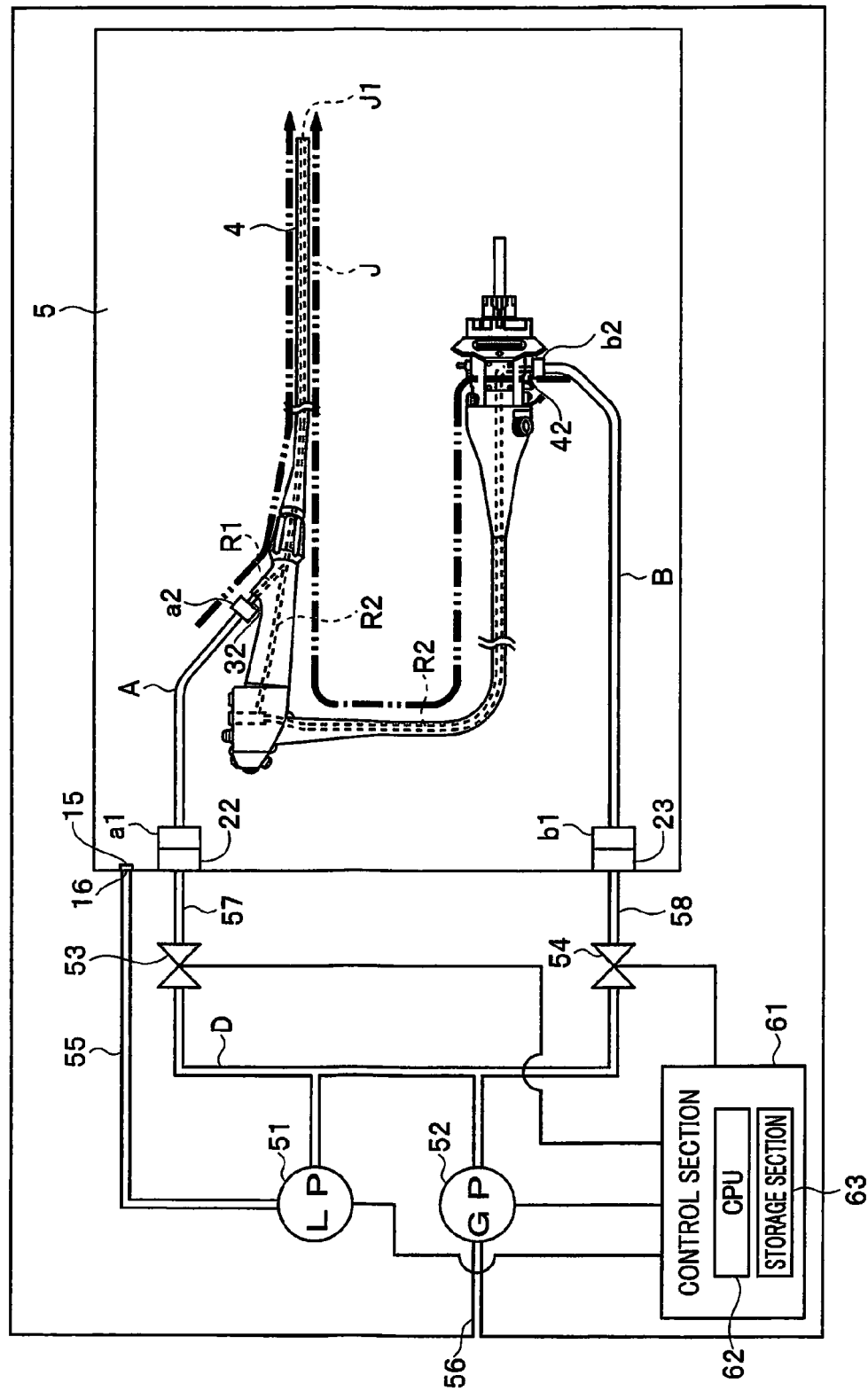
FIG. 6 is an explanatory view describing first control of the endoscope reprocessor according to the embodiment of the present invention.
Figure 7:
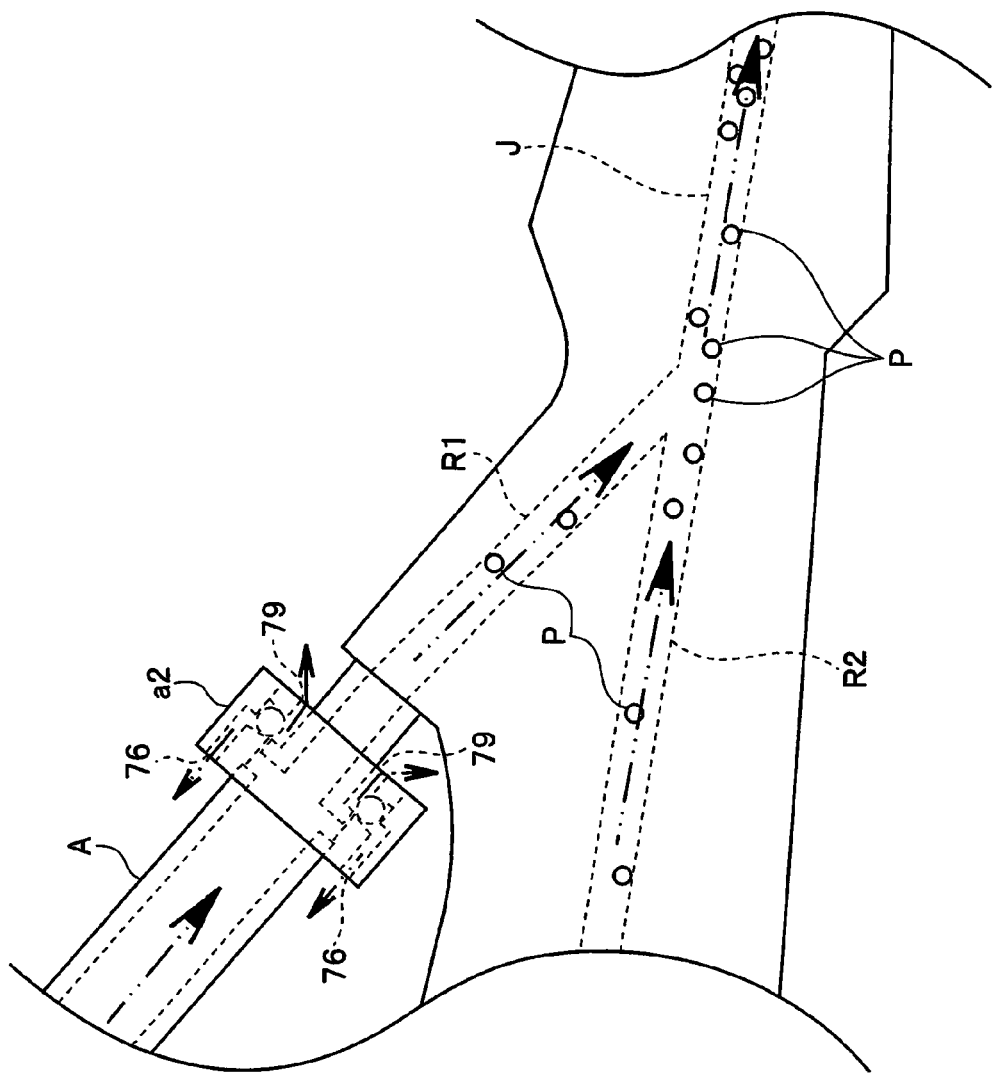
FIG. 7 is an enlarged explanatory view of the merging section for describing fluid transmission based on the first control of the endoscope reprocessor according to the embodiment of the present invention.

Drive of the endoscope reprocessor 1 in the first control and a flow in the endoscope conduit associated with the drive will be described with reference to FIGS. 6 and 7.

In the first control, the first fluid supply section I and the second fluid supply section II are driven at the same time as described above. Therefore, the first electromagnetic valve 53 and the second electromagnetic valve 54 of the endoscope reprocessor 1 are opened, and the fluid is discharged from the forceps plug port 22 and the suction pipe sleeve port 23.

The forceps plug port 22 communicates with the forceps plug pipe sleeve 32 of the endoscope 4 through the cleaning tube A, and the fluid discharged from the forceps plug port 22 is introduced to the treatment instrument channel J from the forceps plug pipe sleeve 32. Subsequently, the fluid is discharged to the outside of the endoscope 4 from the opening J1 of the treatment instrument channel distal end.

The suction pipe sleeve port 23 communicates with the suction pipe sleeve 42 of the endoscope 4 through the cleaning tube B, and the fluid discharged from the suction pipe sleeve port 23 is introduced to the suction conduit R2 from the suction pipe sleeve 42. Subsequently, since the suction conduit R2 is connected to the middle position of the treatment instrument channel proximal end side R1, the fluid introduced from the suction pipe sleeve 42 moves to the treatment instrument channel J, and the fluid is discharged to the outside of the endoscope 4 from the opening J1 of the treatment instrument channel distal end.

In the first control, the fluid is also supplied from the forceps plug pipe sleeve 32. This can prevent the fluid flown from the suction conduit R2 to the treatment instrument channel J from entering the treatment instrument channel proximal end side R1 and can prevent the wastes P existing in the treatment instrument channel proximal end side R1 from being pushed out toward the forceps plug pipe sleeve 32.

By performing the first control, the wastes P existing in the treatment instrument channel proximal end side R1 are discharged to the outside of the endoscope 4 from the opening J1 of the treatment instrument channel J.

Figure 8:
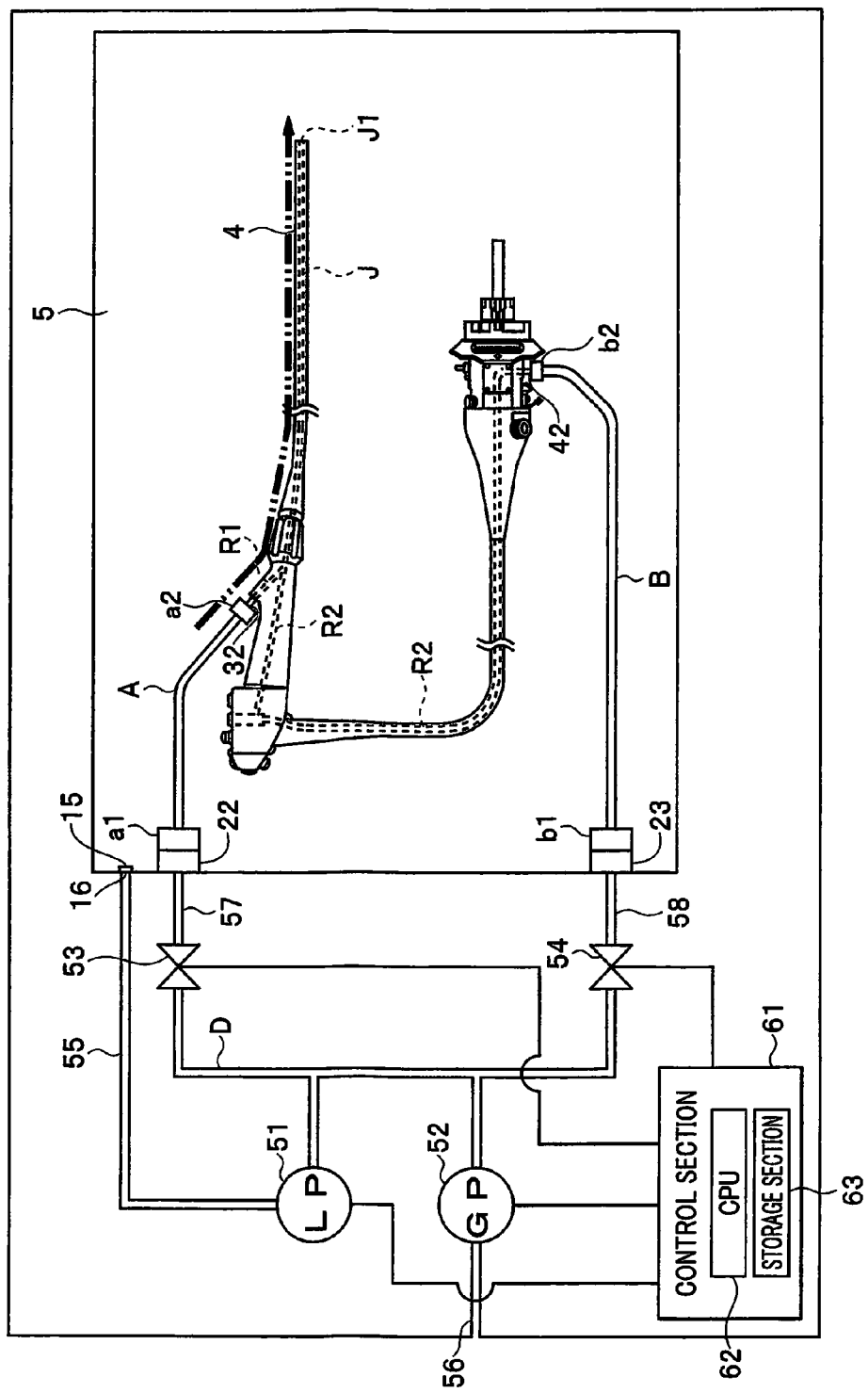
FIG. 8 is an explanatory view describing second control of the endoscope reprocessor according to the embodiment of the present invention.
Figure 9:
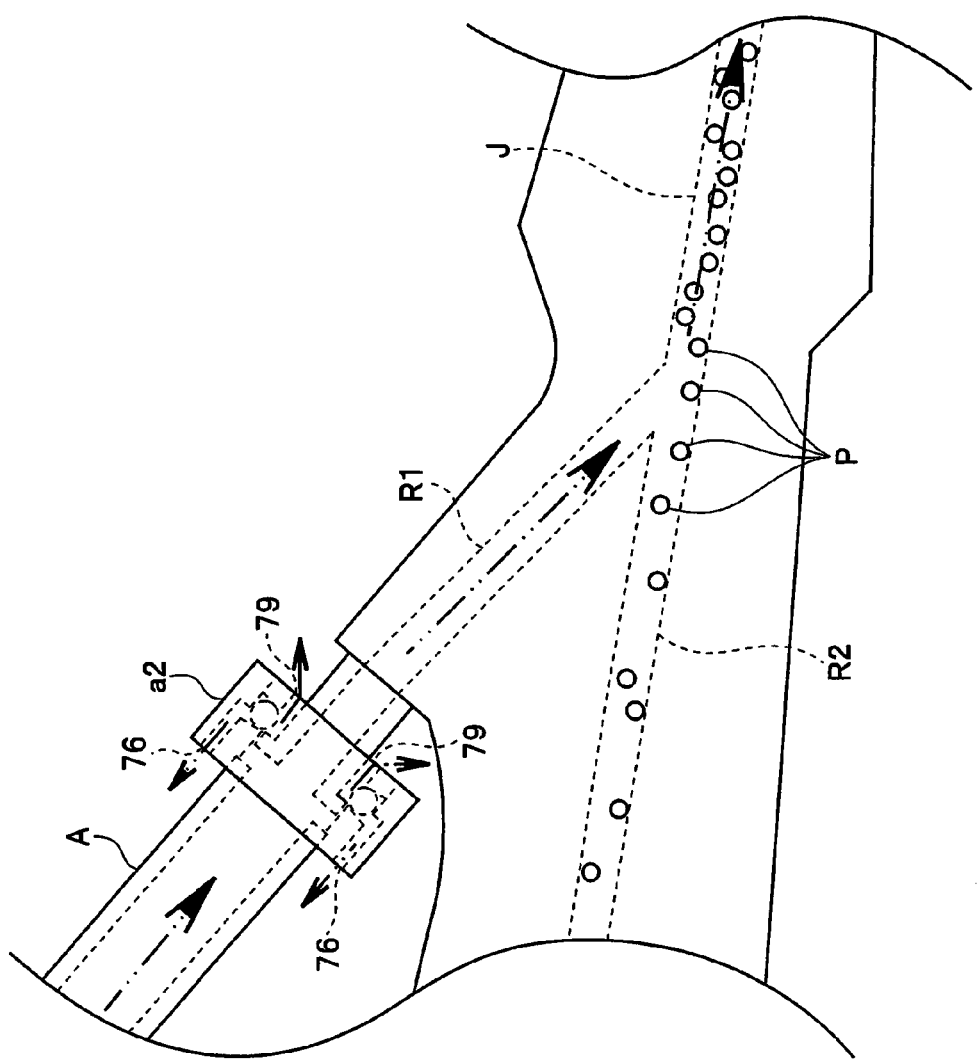
FIG. 9 is an enlarged explanatory view of the merging section for describing fluid transmission based on the second control of the endoscope reprocessor according to the embodiment of the present invention.

Drive of the endoscope reprocessor 1 in the second control and a flow in the endoscope conduit associated with the drive will be described with reference to FIGS. 8 and 9.

In the second control, the first fluid supply section I is driven, and the second fluid supply section II is halted as described above. Therefore, the first electromagnetic valve 53 of the endoscope reprocessor 1 is opened, and the fluid is discharged from the forceps plug port 22. The second electromagnetic valve 54 of the endoscope reprocessor 1 is closed or narrowed such that the flow rate becomes lower than the flow rate of the first fluid supply section I.

In the second control, the second electromagnetic valve 54 is closed or narrowed. This can prevent the fluid flown from the suction conduit R2 to the treatment instrument channel J from entering the treatment instrument channel proximal end side R1 and can prevent the wastes P existing in the treatment instrument channel proximal end side R1 from being pushed out toward the forceps plug pipe sleeve 32.

By performing the second control, the wastes P existing in the treatment instrument channel proximal end side R1 are discharged to the outside of the endoscope 4 from the opening J1 of the treatment instrument channel J.

When the gas-liquid two-phase flow is performed as the second control, the first electromagnetic valve 53 is opened, and the second electromagnetic valve 54 is closed. In this state, the liquid pump 51 is driven to fill the treatment instrument channel J with the liquid. Next, the first electromagnetic valve 53 is opened, and the second electromagnetic valve 54 is closed. In this state, the liquid pump 51 is halted, and the gas pump 52 is driven.

As a result, the liquid filling the treatment instrument channel J is pushed out by the gas, and in this case, the gas-liquid two-phase flow is generated in the treatment instrument channel J.

Figure 11:
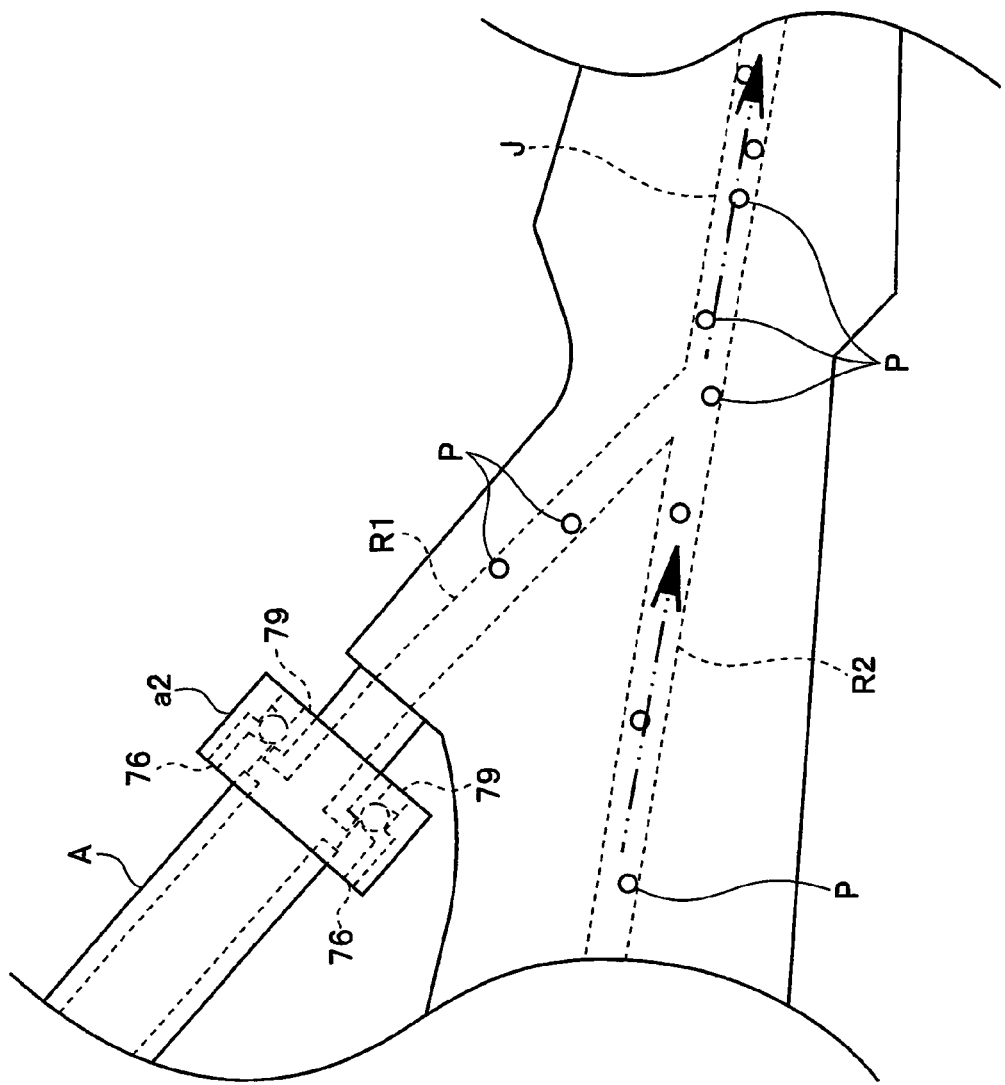
FIG. 11 is an enlarged explanatory view of the merging section for describing fluid transmission based on the third control of the endoscope reprocessor according to the embodiment of the present invention.
Figure 12:
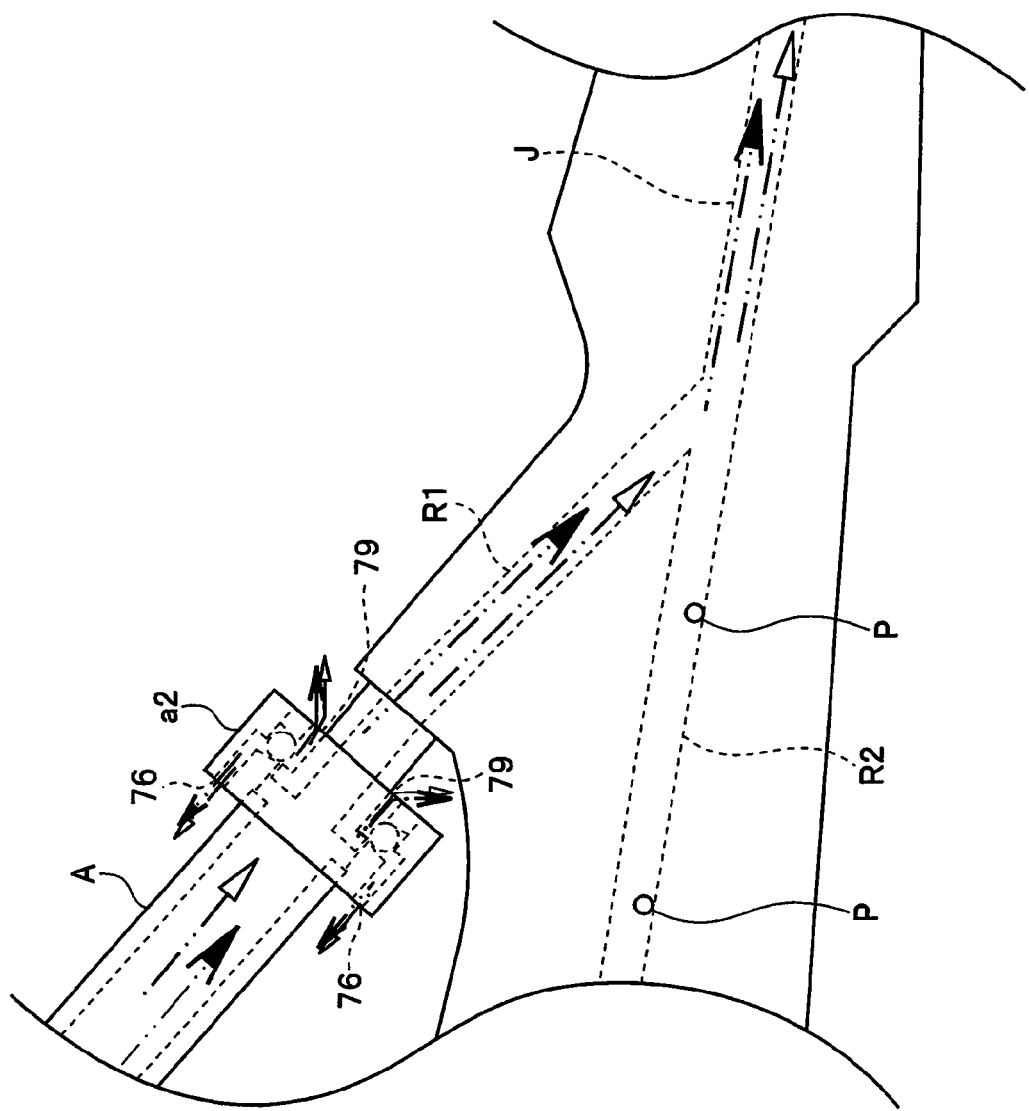
FIG. 12 is an explanatory view describing a gas-liquid two-phase flow based on the second control of the endoscope reprocessor according to the embodiment of the present invention.
Figure 13:
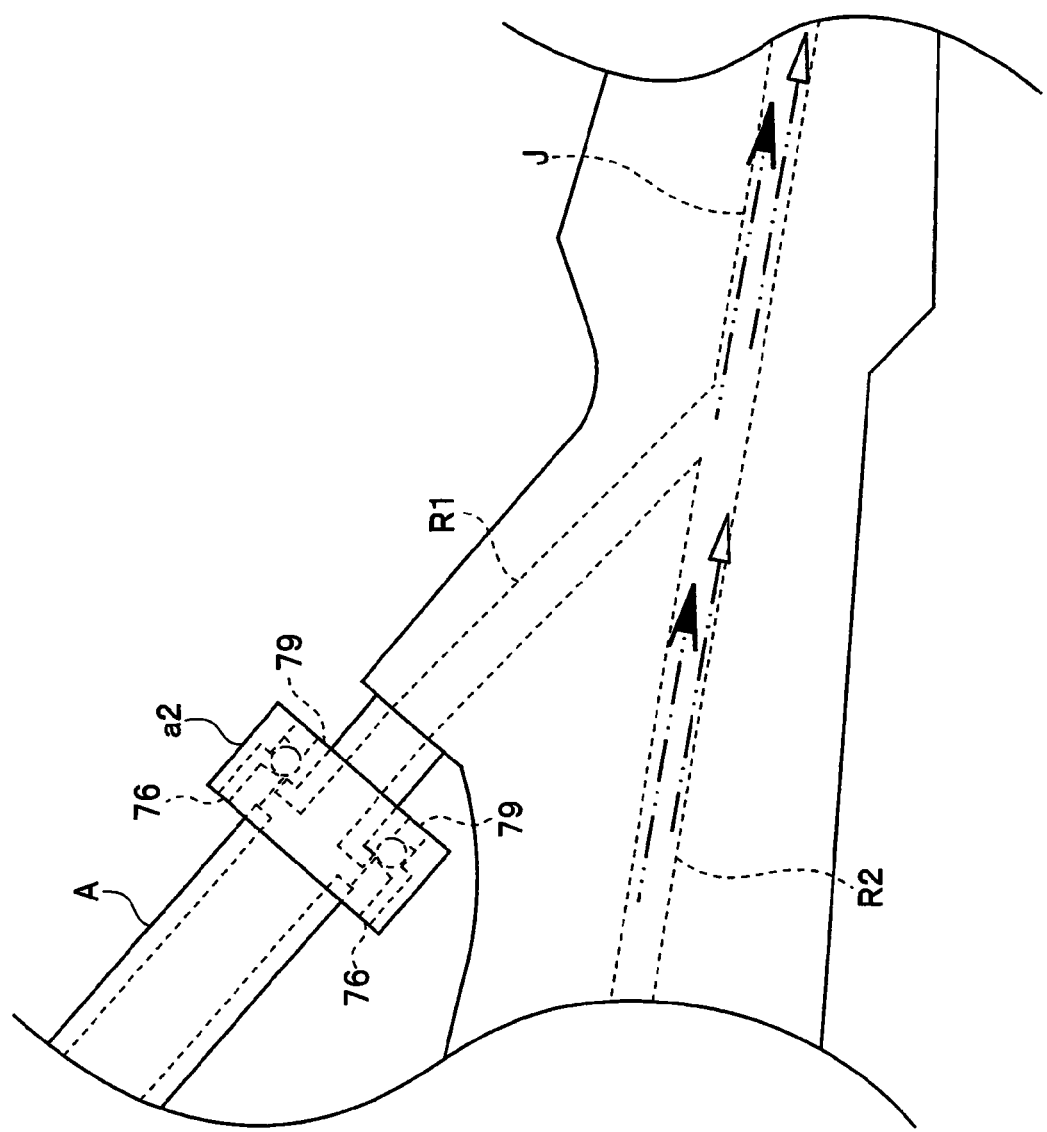
FIG. 13 is an explanatory view describing a gas-liquid two-phase flow based on the third control of the endoscope reprocessor according to the embodiment of the present invention.

Drive of the endoscope reprocessor 1 in the third control and a flow in the endoscope conduit associated with the drive will be described with reference to FIGS. 10 and 11.

In the third control, the second fluid supply section II is driven, and the first fluid supply section I is halted as described above. Therefore, the second electromagnetic valve 54 of the endoscope reprocessor 1 is opened, and the fluid is discharged from the suction pipe sleeve port 23. The first electromagnetic valve 53 of the endoscope reprocessor 1 is closed or narrowed such that the flow rate becomes lower than the flow rate of the second fluid supply section II.

Before the third control is carried out, at least one of the first control and the second control is carried out, and the wastes P in the treatment instrument channel proximal end side R1 are discharged. In this state, the wastes P are not pushed out toward the forceps plug pipe sleeve 32 even when the third control is carried out.

When the gas-liquid two-phase flow is performed as the third control, the second electromagnetic valve 54 is opened, and the first electromagnetic valve 53 is closed. In this state, the liquid pump 51 is driven to fill the treatment instrument channel J with the liquid. Next, the second electromagnetic valve 54 is opened, and the first electromagnetic valve 53 is closed. In this state, the liquid pump 51 is halted, and the gas pump 52 is driven.

As a result, the liquid filling the suction conduit R2 and the treatment instrument channel J is pushed out by the gas, and in this case, the gas-liquid two-phase flow is generated in the suction conduit R2 and the treatment instrument channel J.

Note that the liquid pump 51 is connected to the circulation port 16 of the treatment tank 5 to import the cleaning liquid from the circulation port 16 in the embodiment. However, the liquid pump 51 may be connected to the cleaning liquid tank to import the cleaning liquid, may be connected to the disinfectant liquid tank to import the disinfectant liquid, or may be connected to the water faucet through the water supply hose connection port 7 to import water, for example.

Note that the embodiment is applied to the cleaning process of the endoscope 4. However, other than the cleaning process of the endoscope 4, the embodiment may be applied to a disinfecting process or a rinsing process of the endoscope 4, for example.

The present invention is not limited to the embodiment, and various changes, modifications, and the like can be made without changing the scope of the present invention.

The present invention can provide an endoscope reprocessor that can reduce catching of contaminants between the pipe sleeve of the endoscope and the connector of the cleaning tube and that can more efficiently execute processing, such as cleaning/disinfecting, of the endoscope.

What is claimed is:

1. An endoscope reprocessor comprising:
   a first fluid supply comprising a liquid pump, a gas pump and a first valve in communication with the liquid pump and the gas pump, the first fluid supply configured to communicate with a forceps plug pipe sleeve of an endoscope to supply a fluid, a gas, or both a fluid and a gas;
   a second fluid supply comprising the liquid pump, the gas pump and a second valve in communication with the liquid pump and the gas pump, the second fluid supply configured to communicate with a suction pipe sleeve of the endoscope to supply a fluid, a gas, or both a fluid and a gas; and
   a controller connected to the liquid pump, the gas pump, the first valve and the second valve, the controller configured to control the first fluid supply and the second fluid supply, wherein
   the controller configured to drive at least one of the liquid pump and the gas pump, the controller configured to perform one of:
      a first performance of driving the first fluid supply and the second fluid supply at a same time;
      a second performance of driving the first fluid supply to supply the fluid, the gas, or the fluid and the gas while:
         not driving the second fluid supply by configuring the second valve into a closed position or
         controlling a flow rate of the second fluid supply to be lower than a flow rate of the first fluid supply by configuring the second valve into a partially open position, which is less open than an open position of the first valve; and
      a third performance of driving the second fluid supply to supply, the fluid, the gas, or the fluid and the gas while:
         not driving the first fluid supply by configuring the first valve into a closed position or
         controlling the flow rate of the first fluid supply to be lower than the flow rate of the second fluid supply by configuring the first valve into a partially open position, which is less open than an open position of the second valve and driving the second fluid supply, after the first performance or the second performance.

2. The endoscope reprocessor according to claim 1, wherein
   the third performance is performed after the second performance.

3. The endoscope reprocessor according to claim 1, wherein
   in the second performance,
   the first fluid supply is driven to fill a conduit of the endoscope with the liquid in a state that the second fluid supply is halted or driven, and then
   the first fluid supply is driven to fill the conduit of the endoscope with the gas in the state that the second fluid supply is halted.

4. The endoscope reprocessor according to claim 3, wherein
   in the third performance,
   the second fluid supply is driven to fill the conduit of the endoscope with the liquid in a state that the first fluid supply is halted or driven, and then
   the second fluid supply is driven to fill the conduit of the endoscope with the gas in the state that the first fluid supply is halted.

* * * * *